US011020743B2

(12) United States Patent
Kauffmann

(10) Patent No.: US 11,020,743 B2
(45) Date of Patent: Jun. 1, 2021

(54) DIAGNOSTIC ASSAY CARTRIDGE FOR CONDUCTING MULTIPLE DIAGNOSTIC ASSAYS ON A PATIENT'S SINGLE LIQUID TEST SAMPLE AND METHODS OF USE RELATED THERETO

(71) Applicant: Siemens Healthcare Diagnostics Inc., Tarrytown, NY (US)

(72) Inventor: Aaron Kauffmann, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/968,717

(22) PCT Filed: Feb. 13, 2019

(86) PCT No.: PCT/US2019/017820
§ 371 (c)(1),
(2) Date: Aug. 10, 2020

(87) PCT Pub. No.: WO2019/160930
PCT Pub. Date: Aug. 22, 2019

(65) Prior Publication Data
US 2020/0368746 A1    Nov. 26, 2020

Related U.S. Application Data

(60) Provisional application No. 62/631,058, filed on Feb. 15, 2018.

(51) Int. Cl.
*B01L 3/00*     (2006.01)
*G01N 33/49*    (2006.01)

(52) U.S. Cl.
CPC ........ *B01L 3/502715* (2013.01); *G01N 33/49* (2013.01); *B01L 2200/028* (2013.01); *B01L 2200/10* (2013.01); *B01L 2200/16* (2013.01); *B01L 2300/0681* (2013.01); *B01L 2300/087* (2013.01); *B01L 2300/123* (2013.01); *B01L 2400/0457* (2013.01)

(58) Field of Classification Search
CPC ................................................ B01L 3/502715
See application file for complete search history.

(56) References Cited

U.S. PATENT DOCUMENTS

| 5,275,951 A * | 1/1994 | Chow ................... B01L 3/0262 |
| | | 137/392 |
| 2004/0070763 A1 * | 4/2004 | Yeung .............. G01N 27/44782 |
| | | 356/436 |
| 2009/0065357 A1 | 3/2009 | Glezer et al. |
| 2011/0104731 A1 * | 5/2011 | Teng ...................... B01L 3/502 |
| | | 435/29 |

(Continued)

FOREIGN PATENT DOCUMENTS

WO    2018017332 A1    1/2018

OTHER PUBLICATIONS

International Search Report and Written Opinion of International Application No. PCT/US2019/017820 dated May 8, 2019.

(Continued)

*Primary Examiner* — Matthew D Krcha
(74) *Attorney, Agent, or Firm* — Andrew Chien

(57) ABSTRACT

Devices, kits, and methods for conducting a plurality of diagnostic assays on a patient's single liquid test sample within a single reaction cassette.

20 Claims, 7 Drawing Sheets

(56) References Cited

U.S. PATENT DOCUMENTS

2013/0331298 A1 12/2013 Rea
2015/0152480 A1 6/2015 Idegami et al.
2016/0266099 A1 9/2016 Price et al.
2017/0036207 A1 2/2017 Wright et al.
2018/0029033 A1 2/2018 Koser et al.

OTHER PUBLICATIONS

Office Action of European Application No. 19754597.3 dated Mar. 18, 2021.

* cited by examiner

DIAGNOSTIC ASSAY CARTRIDGE FOR CONDUCTING MULTIPLE DIAGNOSTIC ASSAYS ON A PATIENT'S SINGLE LIQUID TEST SAMPLE AND METHODS OF USE RELATED THERETO

CROSS REFERENCE TO RELATED APPLICATIONS

This application claims priority to U.S. Provisional Application No. 62/631,058, filed Feb. 15, 2018, the disclosure of which is hereby incorporated by reference in its entirety.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) for conducting more than one diagnostic assay on a patient's single liquid test sample. More specifically, the presently disclosed and claimed inventive concept(s) relate to embodiments of an improved reaction cassette that separates a patient's single liquid test sample (and reaction buffer(s)) into at least two separate subsamples for the conductance of at least two diagnostic assay(s) within the improved reaction cassette, as well as kits and methods of use related thereto.

BACKGROUND

Numerous devices and methods exist for detecting analytes that may be present in a patient's liquid/fluid test sample. Such devices have been proven to be effective in diagnostic assays that detect the presence and quantity of certain analytes indicative of a patient's health, including, but not limited to, glycated hemoglobin (HbA1c), microalbumin and creatinine, and lipid-based analytes, such as cholesterol, triglycerides, and/or high-density lipoproteins. However, these devices, kits, and methods are limited in the number diagnostic assays that can be performed for the detection of such analytes. Such devices, kits, and methods, for instance, may be limited in the number of reagents (both solid and liquid) that can be employed in a given assay(s). In addition, such instruments for conducting the assay(s) may utilize the entire volume of the patient's liquid test sample in the conductance of a single assay. Accordingly, a need exists for new and improved devices, kits, and methods that allow for multiple diagnostic assays to be performed in a single reaction cassette on a patient's single liquid test sample. Such devices, kits, and methods thereby allow, by way of example and not by way of limitation, for: (1) an increase in the number of analytes that can be detected in a patient's single liquid test sample; and (2) the ability to conduct multiple diagnostic assays on a patient's single liquid test sample within the improved reaction cassette. It is to such devices and methods, as well as kits related thereto, that the presently disclosed and claimed inventive concept(s) is directed.

DETAILED DESCRIPTION

Figure 1:
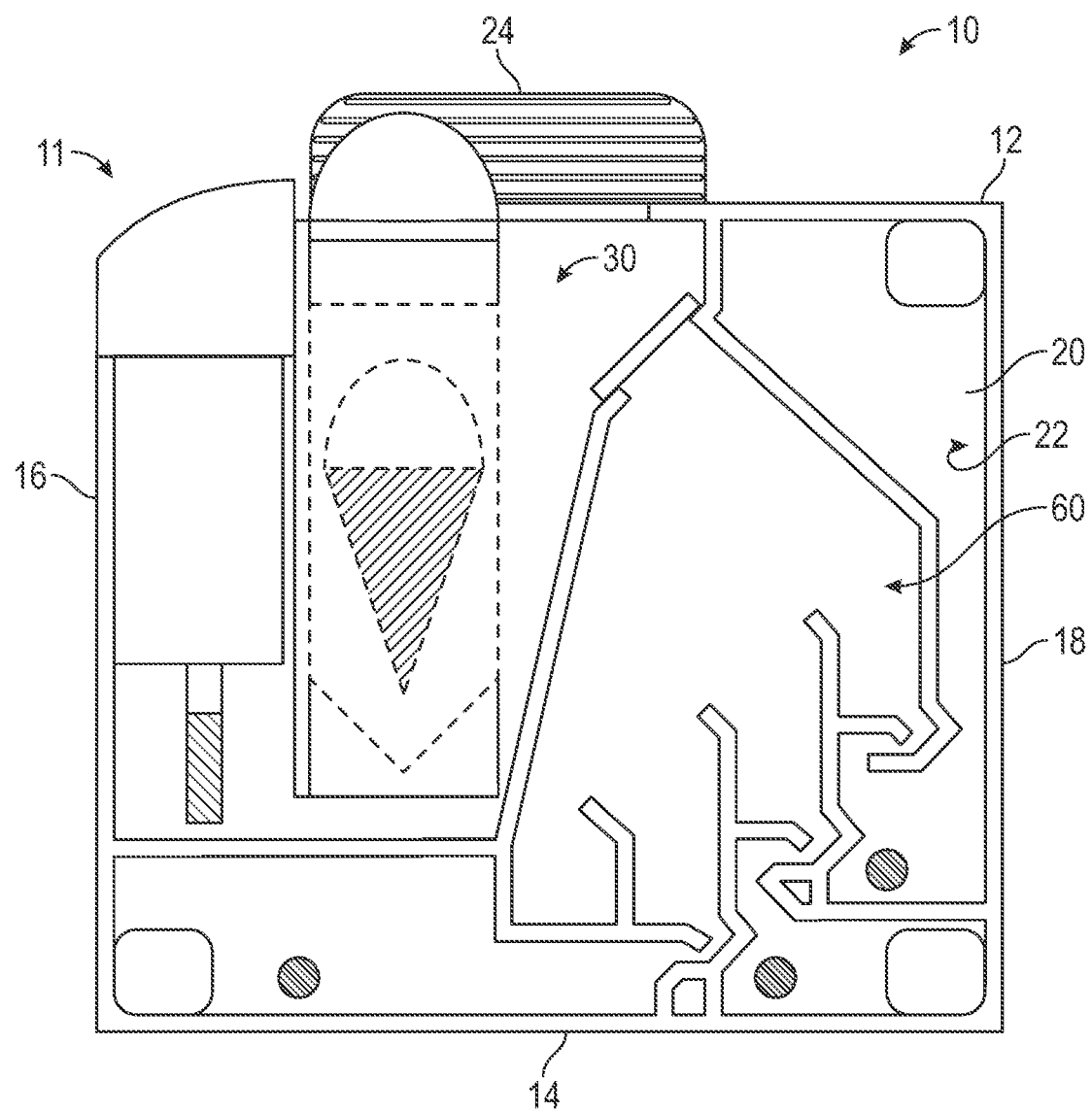
FIG. 1 is a top view of one non-limiting embodiment of an improved reaction cassette constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the sample utilized in accordance with the presently disclosed and claimed inventive concept(s) is from about 1 to about 100 microliters. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters, or less than or equal to about 40 microliters. In one non-limiting embodiment of the presently disclosed and/or claimed inventive concept(s), the liquid test sample is either whole blood and/or urine.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "reaction cassette" includes any device(s) capable of performing at least one diagnostic assay as described herein. The reaction cassette may perform the diagnostic assay(s) manually, but, in most instances, the reaction cassette will be inserted into a system that automates the performance of the diagnostic assay(s). In one non-limiting embodiment, the reaction cassette is configured for use in automated diagnostic assays conducted by the DCA Vantage® Analyzer commercially available from Siemens Healthcare Diagnostics, Inc.

Turning now to particular embodiments, the presently disclosed and claimed inventive concept(s) relate to a device(s), kit(s), and method(s) for dispensing at least two liquid reagents for use in analyte(s) detection assays. More specifically, the presently disclosed and claimed inventive concept(s) relate to a modified apparatus present within a reaction cassette that is capable of dispensing at least two liquid reagents for use in analyte(s) detection assays, as well as kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radio-immunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radio-immunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any fluid sample, including, without limitation, whole blood, plasma, serum, or urine.

Referring now to the Figures, and more particularly to FIG. 1, shown therein is a non-limiting embodiment of an improved reaction cassette 10 for the conductance of at least two diagnostic assays utilizing a patient's single liquid test sample. As shown in FIG. 1, in one non-limiting embodiment the reaction cassette 10 comprises a body 11 formed by a top perimeter side 12, a bottom perimeter side 14, a first perimeter side 16, a second perimeter side 18, and a bottom portion 22. The reaction cassette 10 further comprises a top portion 20 that is used to seal the body 11 of the reaction cassette 10 following the incorporation of a buffer tray 50 (shown in greater detail in FIG. 2) into the reaction cassette 10. Such seal can be accomplished via any method commonly known in the art, including, without limitation, via adhesive(s), glue, sonic welding, laser welding, and/or any permanent fasteners.

In one non-limiting embodiment, the body 11 of the reaction cassette 10 is constructed such that the body 11 is formed via the connection of the top perimeter side 12, the bottom perimeter side 14, the first perimeter side 16, and the second perimeter side 18 to the bottom portion 22. Such connection can be via any method commonly known in the art, including, without limitation, adhesive(s), glue, sonic welding, laser welding, and/or any permanent fastener(s). In another non-limiting embodiment, the body 11 can be constructed such that the top perimeter side 12, the bottom perimeter side 14, the first perimeter side 16, the second perimeter side 18, and the bottom portion 22 is one contiguous piece, for instance, by way of example only, one contiguous piece of plastic.

The reaction cassette 10 has a substantially horizontal axis of rotation. While the external dimensions of the reaction cassette 10 are not critical, the reaction cassette 10 typically has a height and width of about 3 centimeters to about 15 centimeters and a thickness of about 0.25 centimeters to about 2 centimeters. In one embodiment, the dimensions of the reaction cassette 10 are a height and width of about 6 centimeters and a thickness of about 1 centimeter. While depicted in FIG. 1 as being substantially square in shape, a person having ordinary skill in the art should readily appreciate that the reaction cassette 10 can be of any shape capable of accomplishing the presently disclosed and/or claimed inventive concept(s), provided that the reaction cassette 10 is shaped so that it is capable of being inserted into an automated instrument/system for the conductance of at least one diagnostic assay(s).

As shown in FIG. 1 and as discussed in greater detail herein, the body 11 of the reaction cassette 10 comprises a liquid test sample mixing chamber 30 wherein the patient's liquid test sample is mixed with at least one reaction buffer(s) and a reaction chamber 60 wherein the patient's single liquid test sample is separated into substantially equal in volume subsamples (for instance, by way of example only, three equal subsamples) for the conductance of the same or different diagnostic assays (for instance, by way of example only, three different diagnostic assays). However, a person having ordinary skill in the art should readily appreciate that the subsamples need not be equal in volume, nor must the sample wells be the same or similar in size to accomplish the presently disclosed and/or claimed inventive concept(s).

Figure 2:
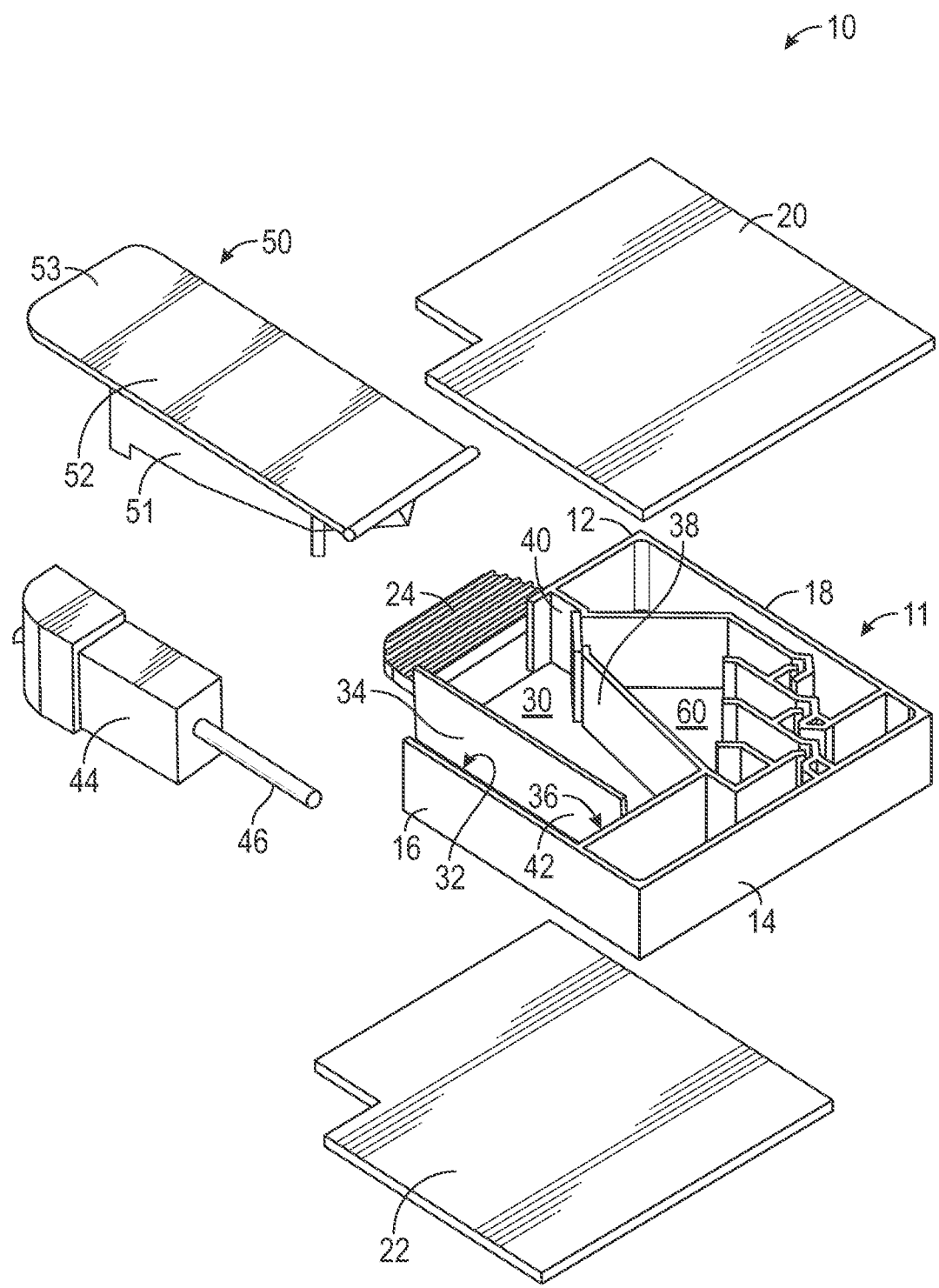
FIG. 2 is an exploded perspective view of one non-limiting embodiment of an improved reaction cassette constructed in accordance with the presently disclosed and/or claimed inventive concept(s).

Referring now to FIG. 2, in one non-limiting embodiment, the body 11 of the reaction cassette 10 further comprises a first interior wall 32, a second interior wall 34, a third interior wall 36, a fourth interior wall 38, and a fifth interior wall 40, wherein the first interior wall 32 and the second interior wall 34 extend downward from the top perimeter side 12 and are positioned opposite of one another and substantially perpendicular to the top perimeter side 12 and the third interior wall 36. The first interior wall 32, together with the third interior wall 36, the fourth interior wall 38, the fifth interior wall 40, the bottom portion 22, and the top portion 52 form the liquid test sample mixing chamber 30, a portion of which is substantially U-shaped. As shown in FIG. 2, the third interior wall 36 acts as the floor of the liquid test sample mixing chamber 30 and extends between (and substantially perpendicular to) the first interior wall 32 and the fourth interior wall 38. The fourth interior wall 38 extends up from the third interior wall 36 and is substantially parallel to the first interior wall 32 (and second interior wall 34). While the Figures depict the liquid test sample mixing chamber 30 as comprising five distinct interior walls, a person having ordinary skill in the art should readily appreciate that the liquid test sample mixing chamber can comprise any number of interior walls capable of accomplishing the presently disclosed and/or claimed inventive concept(s), including, by way of example only, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or greater than or equal to 100 interior walls.

Once the body 11 of the reaction cassette 10 has been sealed by the top portion 20 (following the incorporation of a buffer tray 50 into the reaction cassette 41—discussed in further detail elsewhere herein), an inlet 42 is thereby formed between the first interior wall side 32 and the second interior wall 34, the inlet 42 being substantially parallel to the first interior wall 32 and the second interior wall 34 and extending from top perimeter side 12 downward toward the third interior wall 36 of the body 11 of the reaction cassette 10. The inlet 42 is capable of securely receiving a liquid test sample dispensing device 44 such that the liquid test sample (not shown) is introduced from a capillary 46 of the liquid test sample dispensing device 44 into the liquid test sample mixing chamber 30 (such as, by way of example only, onto the third interior wall 36) of the body 11 of the reaction cassette 10. Accordingly, one non-limiting aspect of the presently disclosed and/or claimed inventive concept(s) contemplates a kit comprising the reaction cassette 10 and the liquid test sample dispensing device 44. While a liquid test sample dispensing device 44 comprising a capillary 46 is shown in the Figures as introducing the liquid test sample into the liquid test sample mixing chamber 30, it should be readily understood to a person having ordinary skill in the art that the liquid test sample can be introduced into the reaction cassette 10 via any device capable of introducing a liquid a test sample, including, by way of example and not by way of limitation, a pipette(s). In addition, the inlet 42 can be stoppered, plugged, or otherwise closed subsequent to the introduction of the liquid test sample into the reaction cassette 10 so as to prevent liquid loss during the course of the methodologies described herein, including, but not limited to, diagnostic assays, including immunoassays.

Figure 3:
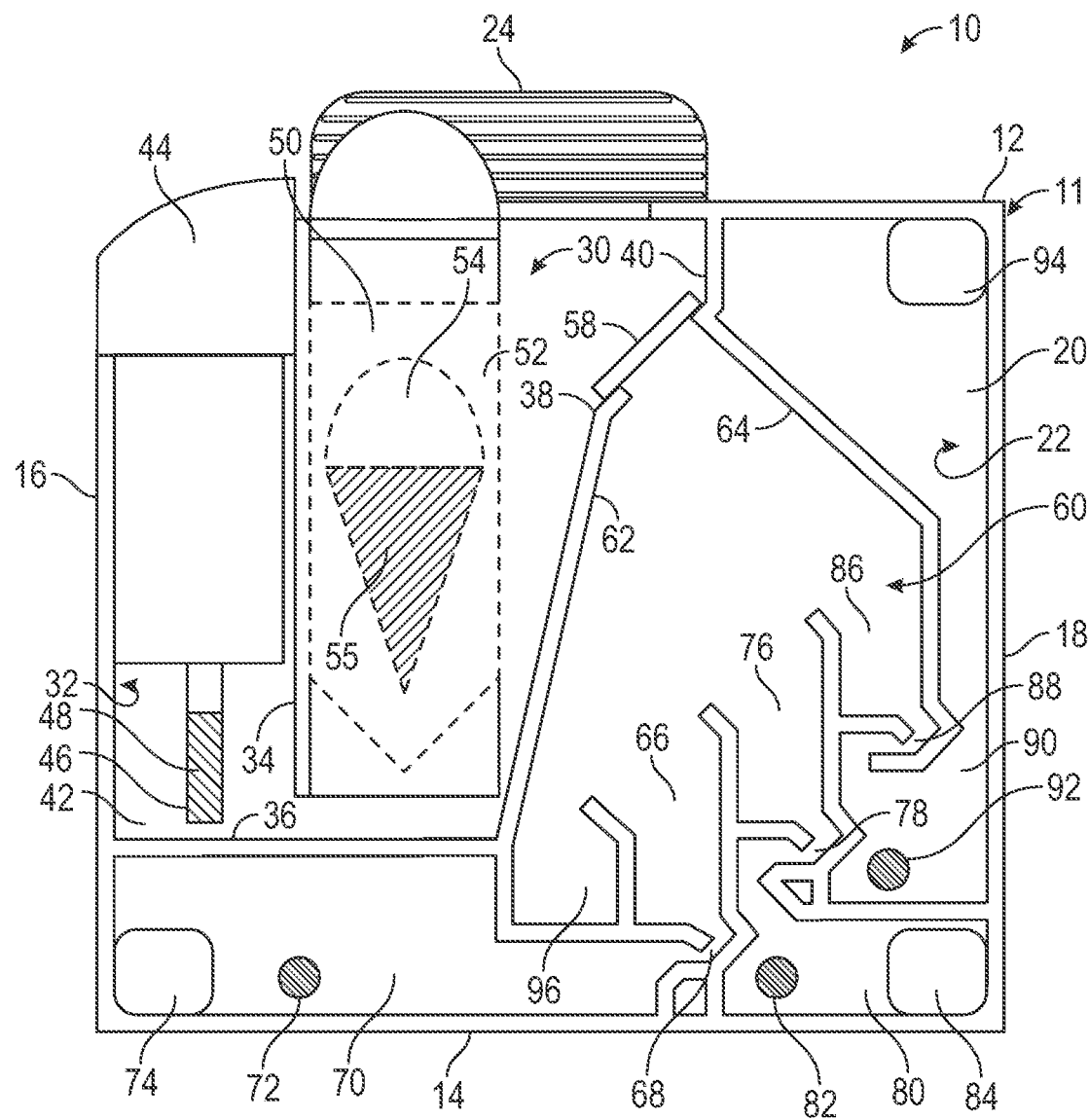
FIG. 3 is a detailed top view of one non-limiting embodiment of the improved reaction cassette of FIG. 1 constructed in accordance with the presently disclosed and/or claimed inventive concept(s).

A buffer tray 50 (shown in greater detail in FIG. 3) is incorporated and secured within the liquid test sample mixing chamber 30 of the body 11 of the reaction cassette 10. The buffer tray 50 comprises a container 51, a flexible cover 52, pull tab portion 53 for selectively removing the flexible cover 52 from the container 51 of the buffer tray 50, and (as shown in FIG. 3) at least buffer well 54 containing at least one buffer 55 (which, in one embodiment, may be, for example, a buffer(s) for conducting one or more diagnostic assays). While the figures depict embodiments of the container 11 having a single buffer well 54 and/or liquid reagent well, it should be readily understood to a person having ordinary skill in the art that the container 51 may be comprised of any number of cavities, buffer agents, and/or liquid reagents. By way of example and not by way of limitation, the container 51 may comprise 1, 2, 3, 4, 5, 6, 7, 8, 9, 10, 15, 20, 50 or any number of cavities capable of being manufactured for incorporation in container 51.

Figure 4A:
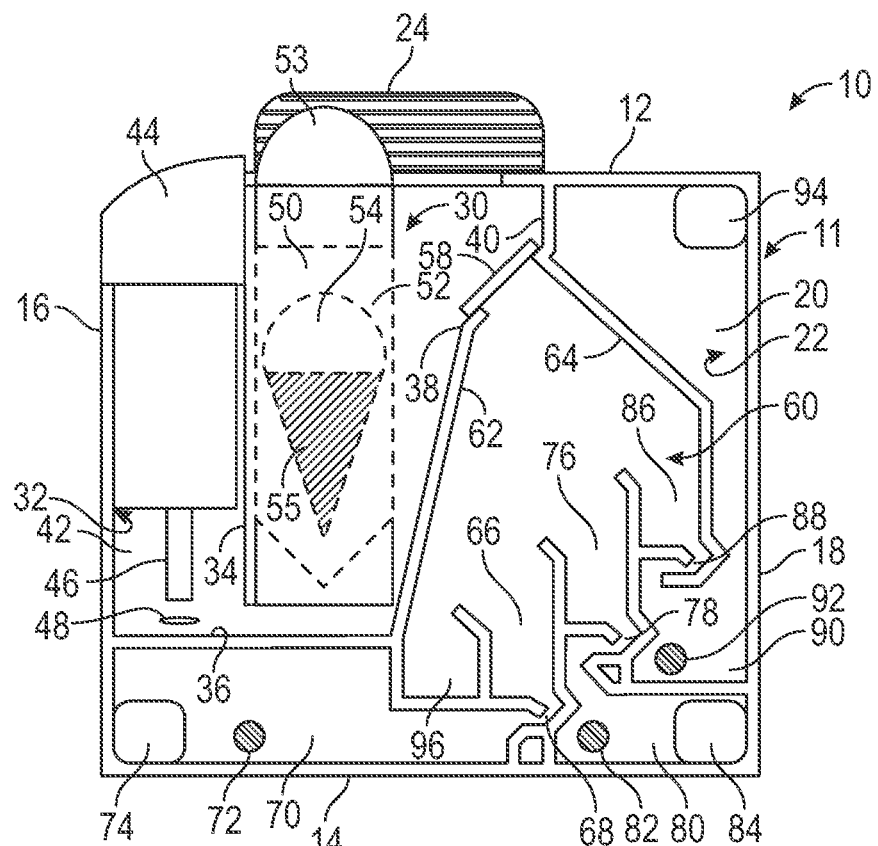
FIGS. 4A-4G are top views of one embodiment of the improved reaction cassette being used to mix a patient's single liquid test sample with at least one reaction buffer and the subsequent separation of the patient's single liquid test sample into three subsamples for the conductance of at least three diagnostic assays within the improved reaction cassette in accordance with the methodologies disclosed and/or claimed herein.
Figure 4B:
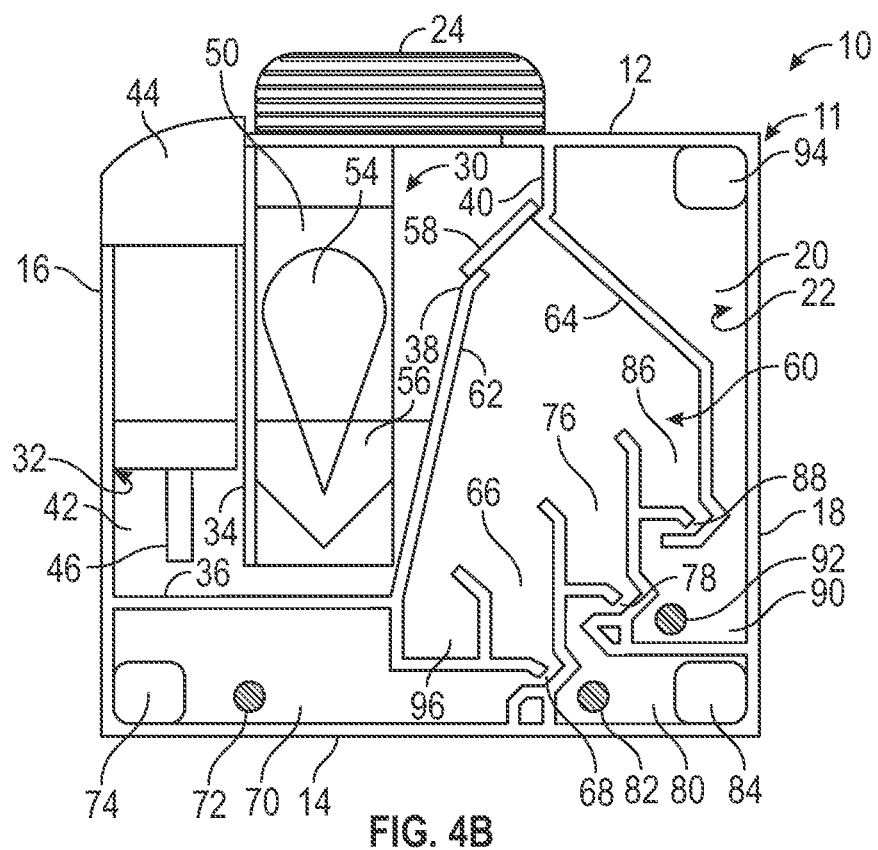

As shown in FIG. 2 (and FIGS. 3-4B) and as further described herein, the flexible cover 52 is removably affixed to the container 51 to seal the container 51 and the at least one buffer well 54, thereby sealing in and preventing the discharge of the at least one buffer 55 from the container 51. The flexible cover 52, when the container 51 is oriented in a substantially vertical position within the liquid test sample mixing chamber 30 of the body 11, can be removed by a user to allow the gravitational dispensing of the at least one buffer 55 from the at least one buffer well 54 so that the at least one buffer 55 can mix with the patient's liquid test sample in preparation for the conductance of at least two diagnostic assays within the reaction cassette 10. The container 51 is preferably fabricated as a molded component formed of a rigid plastic material (so as to avoid deformation of the container 51 upon removal of the flexible cover 52 therefrom by a user), including, for example, high-density polyethylene; however, the container 51 may be constructed of any material capable of accomplishing the presently disclosed and/or claimed inventive concept(s). The flexible cover 52 may be, by way of example only, constructed of a vapor and liquid impermeable material, including, for example, a plastic laminate material or aluminum foil material. In one embodiment, the flexible cover 52 is affixed to the container 51 by a heat-activated peelable adhesive that leaves substantially no residue on the container 51 when the flexible cover 52 is removed by a user. In one embodiment, the flexible cover 52 may be constructed and configured to comprise a pull tab portion 53, which can be grasped and pulled by a user to remove the flexible cover 52 from the container 51 to thereby facilitate the mixing of the at least one buffer 55 with the patient's liquid test sample for the conductance of at least two diagnostic assay within the reaction cassette 10.

Referring now to FIG. 3, shown therein is a detailed top view of the reaction cassette 10 of FIG. 1 constructed in accordance with the presently disclosed and/or claimed inventive concept(s). As shown in FIG. 3, the liquid test sample dispensing device 44 has been inserted into and secured within the inlet 42 and the capillary 46 of the liquid test sample dispensing device 44 contains a previously-collected patient's liquid test sample 48 (for instance, by way of example, a patient's whole blood sample). In addition, the buffer tray 50 has been inserted and secured within the liquid test sample mixing chamber 30. As discussed further herein, once the patient's liquid test sample 48 is dispensed from the liquid test sample dispensing device 44 into the liquid test sample mixing chamber 30, the liquid test sample 48 mixes with the at least one buffer 55 (after the flexible cover 52 has been removed from the buffer tray 50) thereby forming a mixed liquid test sample 56 at which point the mixed liquid test sample 56 is ready to pass through the filter 58 into the reaction chamber 60 for the conductance of at least two diagnostic assays.

In one non-limiting embodiment and as shown in FIG. 3 and subsequent figures, the liquid test sample mixing chamber 30 and the reaction chamber 60 are separated by at least one filter 58; however, it should be readily understood to a person having ordinary skill in the art that the reaction cassette 10 need not comprise the filter 58 to accomplish the presently disclosed and/or claimed inventive concept(s). When used, the at least one filter 58 both ensures that no debris passes into the reaction chamber 60 from the liquid test sample mixing chamber 30 and, as shown in greater detail in FIGS. 4A-4G, only the mixed liquid test sample 56 enters through the filter 58 into the reaction chamber 60. The at least one filter 58 can be constructed of any material(s) capable of accomplishing the presently disclosed and/or claimed inventive concept(s), including, without limitation, filter paper and/or a mesh filter.

As depicted in FIG. 3, the reaction chamber 60 comprises a first interior wall 62, a second interior wall 64, a first sample well 66, a second sample well 76, a third sample well 86, and a sample spill-over well 96. While shown in FIG. 3 as comprising two interior walls, 62 and 64, three sample wells 66, 76, and 86, and a single sample spill-over well 96, a person having ordinary skill in the art should readily appreciate that the reaction chamber 60 may comprise any number of interior walls, sample wells, and spill-over wells capable of accomplishing the presently disclosed and/or claimed inventive concept(s), including, without limitation, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or greater than or equal to 100 of each of the interior walls, sample well, and spill-over wells. After the mixed liquid test sample 56 (which comprises the liquid test sample 48 mixed with the buffer 55) passes through the filter 58 into the reaction chamber 60, it is separated into distinct, substantially equal volumes of subsamples, the number of subsamples corresponding directly to the number of sample wells comprising the reaction chamber 60. In one non-limiting embodiment, and as shown in greater detail in FIGS. 4A-4G, the mixed liquid test sample 56 is separated into three distinct subsamples represented as 56A, 56B, and 56C (with the excess mixed liquid test sample 56 (represented as 56D) residing in the sample spillover well 96). As discussed further herein, the mixed liquid test subsamples 56A, 56B, and 56C enter the first sample well 66, the second sample well 76, and the third sample well 86, respectively, via rotation of the reaction cassette 10 about a substantially horizontal axis within an automated diagnostic assay instrument. As indicated above, any excess mixed liquid test sample 56 enters and resides in the sample spill-over well 96.

While the description herein below is in reference to the first sample well 66, such description is deemed wholly relevant to the structure and functioning of the second sample well 76 and third sample well 86 (and any sample well of the presently disclosed and/or claimed inventive concept(s)). Accordingly, for purposes of brevity and to avoid unnecessary repetition, only the structure and function of the first sample well 66 is described.

In one non-limiting embodiment, the first sample well 66 comprises a first bubble pit 68, a first sample reaction chamber 70, a first solid reagent zone 72, and a sample read window 74. While shown in the Figures as comprising three solid reagent zones (the first solid reagent zone 72, a second solid reagent zone 82, and a third solid reagent zone 92), it should be understood to a person having ordinary skill in the art that the reaction cassette 10 can comprise any number of solid reagent zones capable of accomplishing the presently disclosed and/or claimed inventive concept(s), including, without limitation, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or greater than or equal to 100 reaction zones. In addition, while the Figures depict each of the sample reaction chambers (the first sample reaction chamber 70, the second sample reaction chamber 80, and the third sample reaction chamber 90) as comprising a single solid reagent zone, it should be readily understood to a person having ordinary skill in the art that each of the sample reaction chambers may comprise any number of solid reagent zones (which contain any number of solid analytical reagents) capable of accomplishing the presently disclosed and/or claimed inventive concept(s), including, without limitation, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or greater than or equal to 100 solid reagent zones and/or solid analytical reagents. The solid analytical reagents may be the same, different, or a combination of same and different chemicals, compounds, molecules, and/or materials.

Once the patient's first mixed liquid test subsample 56A has entered the first sample well 66, the first mixed liquid test subsample 56A resides and is retained in the first sample well 66 as a result of the first bubble pit 68. The first bubble pit 68 is configured such that the patient's first mixed liquid test subsample 56A stops and is retained at the first bubble pit 68 until agitated (i.e., via agitation of the reaction cassette 10 within the diagnostic assay instrument). Upon agitation, the first mixed liquid test subsample 56A passes from and through the first bubble pit 68 into the first sample reaction chamber 70. Once inside the first sample reaction chamber 70, the first mixed liquid test subsample 56A (facilitated by rotation of the reaction cassette 10 within an automated diagnostic assay instrument) comes into contact with the first solid reagent zone 72.

It should be readily understood that the agitation that releases the mixed liquid test subsamples from the respective sample wells through the respective bubble pits and into the respective sample reaction chambers can cause all of the subsamples to: (1) individually flow into the respective sample reaction chamber one at a time; (2) two or more subsamples may flow simultaneously into their respective sample reaction chambers, while other subsamples remain in their particular sample wells and bubble pits; or (3) all of the subsamples may flow simultaneously into their respective sample reaction chambers.

The solid reagent zones may be used and positioned at any location(s) along the respective sample reaction chamber(s) (for instance, the first sample reaction chamber 70, the second sample reaction chamber 80, and the third sample reaction chamber 90) in order to accomplish the presently disclosed and/or claimed inventive concept(s). In one non-limiting embodiment, the first solid reagent zone 72 is substantially located at a point on the bottom portion 22 of the body 11 wherein the first solid reagent zone 22 is positioned within the first sample reaction chamber 70 such that the first mixed liquid test subsample 56A contacts the first solid reagent zone 72 before interfacing with the first sample read window 74.

The first solid reagent zone 72 (and the second reagent zone 82 and third reagent zone 92) is incorporated with at least one solid analytical reagent(s) for performing particular analytical assay procedures. The at least one solid analytical reagent(s) are, in one embodiment, present in the solid reagent zones in a substantially dry, water soluble, suspendable or dissolvable form, and can be incorporated along the first sample reaction chamber 70 (and/or the second sample reaction chamber 80 and third sample reaction chamber 90) according to methods known in the art, such as, for example, by noncovalent binding techniques, absorptive techniques, and the like. In one embodiment, the solid reagent zones 72, 82, and 92 are defined in the form of substantially flat, raised portions or mesa-shaped nodes on the surface of the selected area of the respective sample reaction chambers 70, 80, and 90 in which the raised upper surface of each node is from about 0.005 inches to about 0.02 inches elevated above a surface of the respective sample reaction chambers 70, 80, and 90.

In accordance with the above, in one non-limiting embodiment, the first sample reaction chamber 70 may comprise a single first solid reagent zone 72 which comprises three solid reagents for accomplishing the presently disclosed and/or claimed inventive concept(s), including, without limitation, assays, including immunoassays. In one non-limiting embodiment, the first solid reagent zone 72 comprises an oxidant (such as, for example, ferricyanide), an agglutinator, and an antibody-latex (for instance, by way of example only, a glycated hemoglobin A1c antibody). However, it should be readily understood to a person having ordinary skill in the art, that any compound, composition, and/or molecule can be incorporated onto and/or in the solid reagent zones in order to accomplish the presently disclosed and/or claimed inventive concept(s), including, without limitation, detection of at least one analyte(s) of interest present in a liquid test sample 48 and the conductance of diagnostic assays, including, without limitation, lipid panel analysis of a patients liquid test sample 48.

The first sample read window 74 can be, by way of example only and not by way of limitation, a transparent cuvette window or an optical window which permits the accurate measurement of detectable signals in the area of the first sample read window 74. Once the patient's first mixed liquid test subsample 56A has contacted and reacted/associated with the at least one solid analytical reagents contained on and within the first solid reagent zone 72, the patient's first mixed liquid test subsample 56A (facilitated in one non-limiting embodiment by the additional rotation of the reaction cassette 10 by the automated diagnostic assay instrument) passes onto the first sample read window 74. Once on the first sample read window 74, such first liquid test subsample 56A is interrogated and produces a detectable signal or signals indicative of the presence and/or quantity and/or concentration of a particular analyte or analytes contained within the patient's first mixed liquid test subsample 56A.

Referring now to FIGS. 4A-4G, shown therein is a non-limiting embodiment of a methodology of conducting at least two diagnostic assays on patient's single liquid test sample 48 utilizing the reaction cassette 10. The flexible cover 52 is present upon insertion of the reaction cassette 10 into the suitable instrument, apparatus, or system and is selectively removed at the appropriate time (as described below) by a user during the conducting of the assay test (i.e., via the user utilizing the pull-tab portion 53 to remove the flexible cover 52). As discussed herein, the various rotation and oscillation movements of the reaction cassette 10 can be performed manually, but in most cases will be performed by a suitable instrument, apparatus, or system, including, without limitation, the DCA Vantage® Analyzer commercially available from Siemens Healthcare Diagnostics, Inc. In addition, as shown in FIGS. 4A-4G, the patient's liquid test sample 48 has been collected in the capillary 46 of the liquid test sample dispensing device 44 and the liquid test sample dispensing device 44 has been inserted into and secured within the inlet 42 of the body 11 of the reaction cassette 10.

In one embodiment, the first step is to provide the reaction cassette 10 into a holder mechanism (not shown) of the above-referenced instrument, apparatus, or system such that bottom perimeter side 14 of the body 11 of the reaction cassette 10 is positioned in a downward orientation within the holder mechanism. Following insertion of the reaction cassette 10 into the suitable instrument, apparatus, or system, a patient's liquid test sample 48 (which has already been collected from a patient and is located in the capillary 46 of the liquid test sample dispensing device 44) is dispensed from the liquid test sample dispensing device 44 such that the liquid test sample 48 resides substantially on the third interior wall 36 and in the liquid test sample mixing chamber 30. Once the patient's liquid test sample 48 has been dispensed into liquid test sample mixing chamber 30, the flexible cover 52 covering the at least one buffer well 54 of the buffer tray 50 is removed (i.e., by a user peeling the flexible cover 52 from the buffer tray 50 via the pull-tab portion 53). Upon removal of the flexible cover 52, the at least one buffer 55 is transported by gravity from the at least one buffer well 54 into the liquid test sample mixing chamber 30 whereby the at least one buffer 55 mixes with the patient's liquid test sample 48 thereby forming a mixed liquid test sample 56.

Figure 4C:
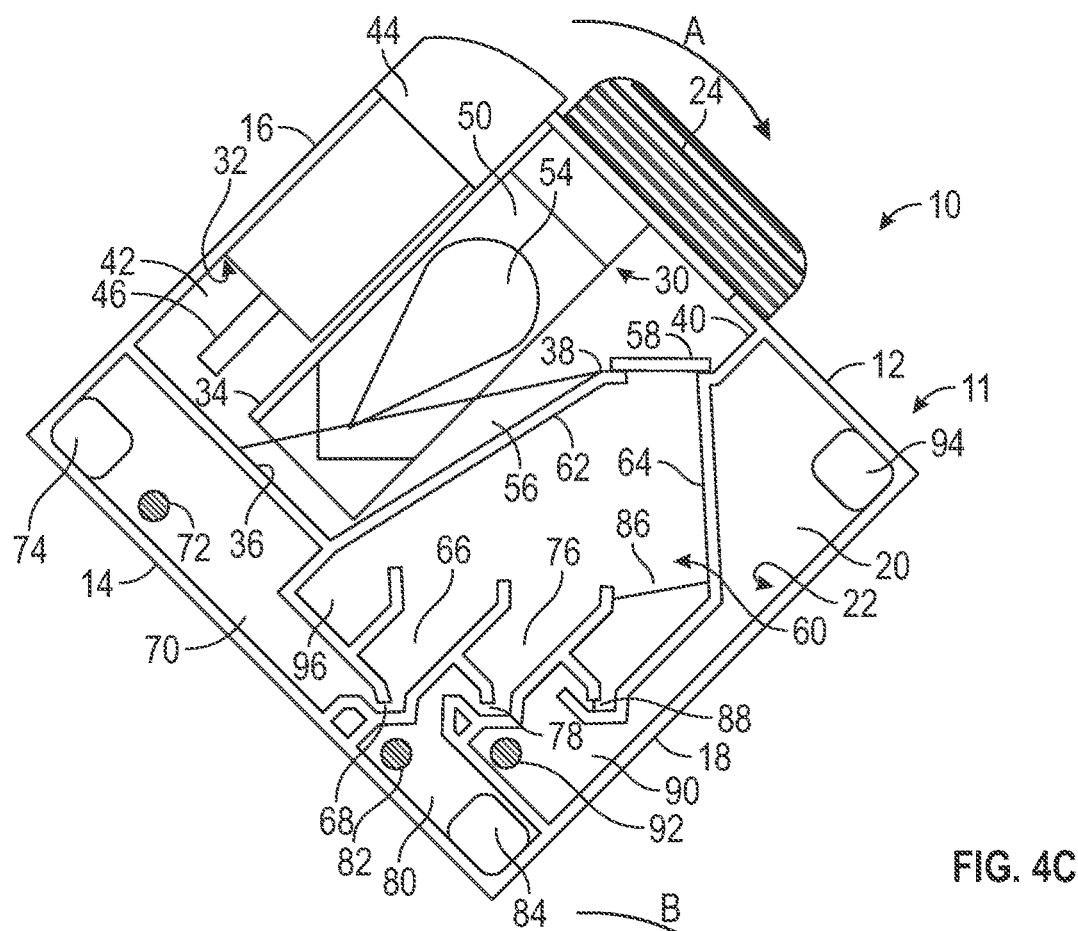
Figure 4D:
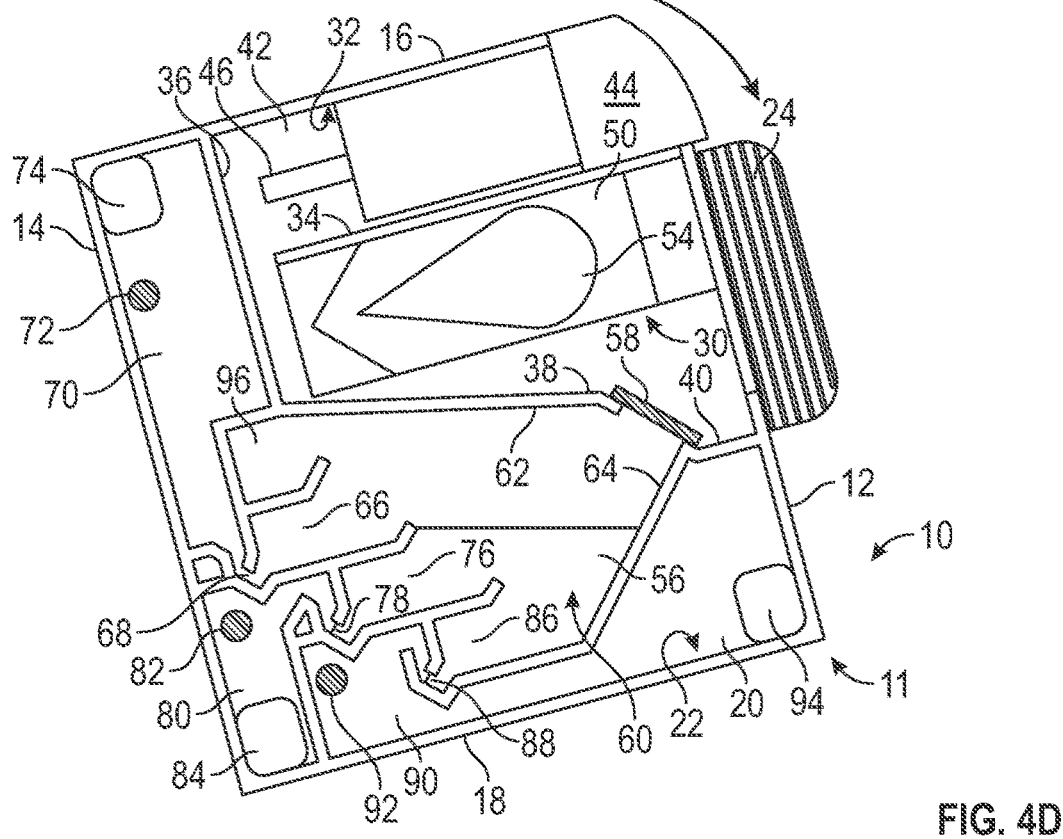

Referring now to FIGS. 4C-4D, following the formation of the mixed liquid test sample 56, the reaction cassette 10 is rotated clockwise (such as, by way of example only, a rotation of about 45°) about a substantially horizontal axis (as shown by solid directional arrow A) within the automated diagnostic assay instrument. As a result of this rotation, the mixed liquid test sample 56 travels up, for instance, the fourth interior wall 38 and through the filter 58 thereby passing into the reaction chamber 60. The reaction cassette 10 is then again rotated clockwise (such as, by way of example only, in a range from about 65° to about 80°) about a substantially horizontal axis (as shown by solid directional arrow B) such that the mixed liquid test sample 56 travels, for instance, along the second interior wall 64 of the reaction chamber 60. As shown in FIG. 4D, at this point the mixed liquid test sample 56 over fills and is substantially contained within the second sample well 76 and the third sample well 86. The mixed liquid test sample 56, while substantially contained within the second sample well 76 and the third sample well 86, does not pass into the second sample reaction chamber 80 or the third sample reaction chamber 90 due to the mixed liquid test sample 56 being stopped by the second bubble pit 78 and the third bubble pit 88, respectively (as described elsewhere herein).

Figure 4E:
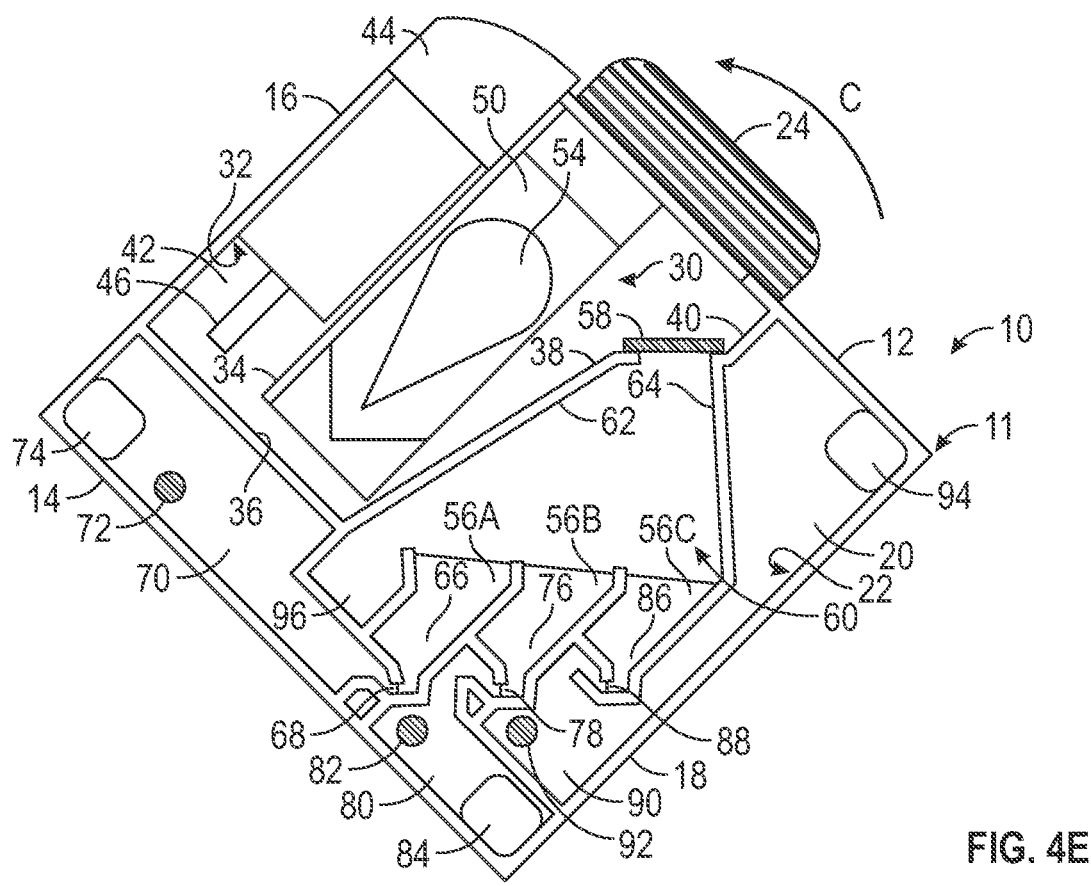
Figure 4F:
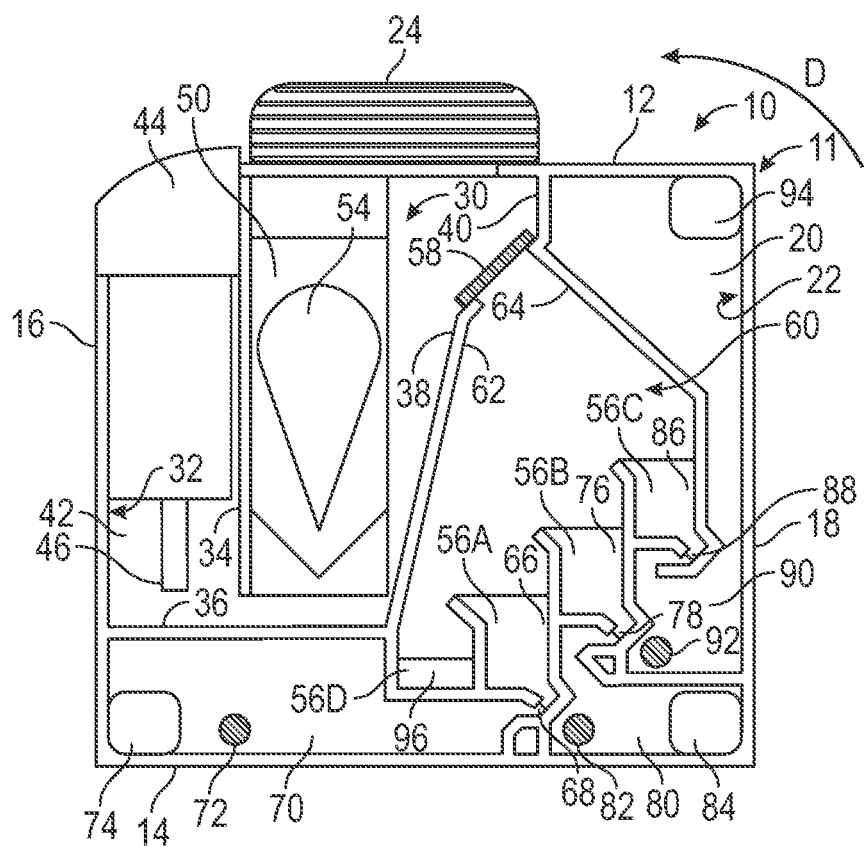

Referring now to FIGS. 4E-4F, the reaction cassette 10 is rotated counter-clockwise (for instance, by way of example only, such that the reaction cassette 10 is rotated to about 45°) about the substantially horizontal axis (as shown by solid directional arrow C). As a result of this counter-clockwise rotation, the mixed liquid test sample 56 is separated into three liquid test subsamples of substantially equal volumes 56A, 56B, and 56C. As shown in FIG. 4E, the first liquid test subsample 56A is retained in the first sample well 66 by the first bubble pit 68; the second liquid test subsample 56B is retained in the second sample well 76 by the second bubble pit 78; and the third liquid test subsample 56C is retained in the third sample well 86 by the third bubble pit 88. The reaction cassette 10 is again rotated counter-clockwise (as shown by solid arrow D) along the horizontal axis such that the reaction cassette 10 is in the substantially original position (i.e., not rotated relative to the horizontal axis). Upon this last rotation, any excess volume of liquid test sample 56 (represented as 56D in FIG. 4F) that overfills the first sample well 66, the second sample well 76, and/or the third sample well 86 is caught and retained within the spill-over well 96. The first liquid test subsample 56A, the second liquid test subsample 56B, and the third liquid test subsample 56C are retained in their respective sample wells via their respective bubble pits. Accordingly, the subsamples are ready to enter their respective sample reaction chambers for the conductance of at least one diagnostic assay.

Figure 4G:
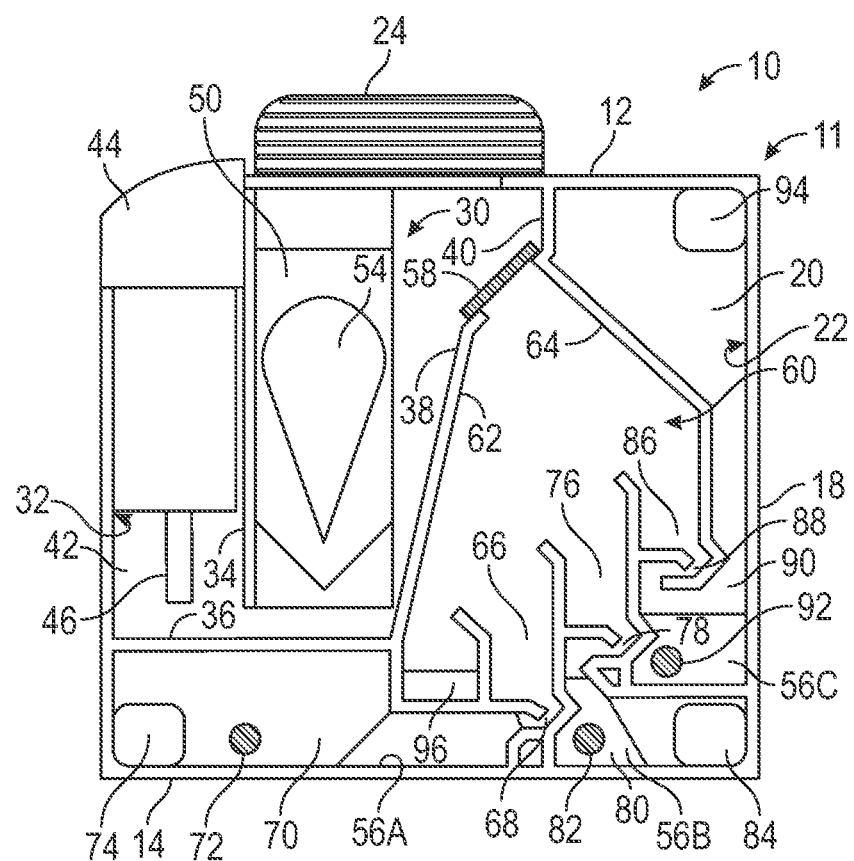

Referring now to FIG. 4G, the reaction cassette 10 is agitated by the diagnostic assay instrument. In one non-limiting embodiment, this agitation results in transfer of air with fluid at the bubble pits, thereby allowing the first liquid test subsample 56A, the second liquid test subsample 56B, and the third liquid test subsample 56C to flow into the first sample reaction chamber 70, the second sample reaction chamber 80, and the third sample reaction chamber 90, respectively. For purposes of brevity, the further methodological steps will only be described with respect to the first liquid test subsample 56A; however, such description is deemed relevant to the performance of at least one diagnostic assay(s) on the second liquid test subsample 56B and the third liquid test subsample 56C (and any liquid test subsample(s) of the presently disclosed and/or claimed inventive concept(s)).

Upon flowing into the first reaction chamber 70, the first liquid test subsample 56A comes into contact and reacts/associates with the first solid reagent zone 72, which comprises at least one solid reagent for conducting at least one diagnostic assay. Following the reaction/association of the first liquid test subsample 56A (or an analyte(s) contained therein) with the first solid reagent zone 72, the first liquid test subsample 56A flows over the first sample read window 74, where it is interrogated and any detectable response resulting from the reaction/association is measured and/or calculated. By way of example only and not by way of limitation, such detectable response may be a total hemoglobin measurement where the liquid test sample 48 is whole blood, for example, such as when performing an assay for the percent and/or concentration of glycated hemoglobin (HbA1c) in a whole blood sample. In the case of a lipid-based assay, such response may be total cholesterol measurement where the liquid test sample 48 is blood serum, for example, when performing an assay for the calculation of the percent and/or concentration of low-density lipoprotein (LDL) cholesterol present in a blood serum sample.

NON-LIMITING EXAMPLES OF THE INVENTIVE CONCEPT(S)

A reaction cassette for the conductance of at least one diagnostic assay, the reaction cassette comprising: a body, the body comprising a top perimeter side, a bottom perimeter side, a first perimeter side, a second perimeter side, a bottom portion, and a top portion, the body further comprising a liquid test sample mixing chamber and a reaction chamber, the liquid test sample mixing chamber and the reaction chamber being separated by a filter, the reaction chamber further comprising at least two sample wells, at least two bubble pits, and at least two sample reaction chambers wherein at least two diagnostic assays are performed on a patient's liquid test sample; an inlet for introducing a liquid test sample into the liquid test sample mixing chamber; and a buffer tray, the buffer tray comprising a container having a buffer well containing at least one buffer, the buffer tray further comprising a flexible cover removably affixed to a top portion of the container to selectively seal the at least one buffer in the buffer tray.

The reaction cassette, wherein the patient's liquid test sample is selected from the group consisting of whole blood and urine.

The reaction cassette, wherein patient's liquid test sample is a 1 microliter volume of whole blood.

The reaction cassette, wherein the at least two diagnostic assays performed within the at least two sample reaction chambers are the same diagnostic assays.

The reaction cassette, wherein the at least two diagnostic assays performed within the at least two sample reaction chambers are different diagnostics assays.

The reaction cassette, wherein the reaction chamber comprises at least three sample reaction chambers.

The reaction cassette, wherein each of the at least two sample reaction chambers further comprise at least one solid reagent zone positioned within each of the at least two sample reaction chambers, each of the at least one solid reagent zone comprising at least one solid analytical reagent.

An analytical reaction kit, the kit comprising: a reaction cassette, the reaction cassette comprising: a body, the body comprising a top perimeter side, a bottom perimeter side, a first perimeter side, a second perimeter side, a bottom portion, and a top portion, the body further comprising a liquid test sample mixing chamber and a reaction chamber, the liquid test sample mixing chamber and the reaction chamber being separated by a filter, the reaction chamber further comprising at least two sample wells and at least two sample reaction chambers wherein at least two diagnostic assays are performed on a patient's liquid test sample; an inlet for introducing a liquid test sample into the liquid test sample mixing chamber; and a buffer tray, the buffer tray comprising a container having a buffer well containing at least one buffer, the buffer tray further comprising a flexible cover removably affixed to a top portion of the container to selectively seal the at least one buffer in the buffer tray; and a capillary, the capillary capable of being partially inserted into the inlet of the reaction cassette to thereby introduce a liquid test sample into the liquid test sample mixing chamber of the reaction cassette.

The analytical reaction kit, wherein the patient's liquid test sample is selected from the group consisting of whole blood and urine.

The analytical reaction kit, wherein patient's liquid test sample is a 1 microliter volume of whole blood.

The analytical reaction kit, wherein the at least two diagnostic assays performed within the at least two sample reaction chambers are the same diagnostic assays.

The analytical reaction kit, wherein the at least two diagnostic assays performed within the at least two sample reaction chambers are different diagnostics assays.

The analytical reaction kit, wherein the reaction chamber comprises at least three sample reaction chambers.

The analytical reaction kit, wherein each of the at least two sample reaction chambers further comprise at least one solid reagent zone positioned within each of the at least two sample reaction chambers, each of the at least one solid reagent zone comprising at least one solid analytical reagent.

A method for performing at least two diagnostic assays on a patient's single liquid test sample, the method comprising the steps of: providing a reaction cassette having a substantially horizontal axis of rotation, a reaction cassette, the reaction cassette comprising: a body, the body comprising a top perimeter side, a bottom perimeter side, a first perimeter side, a second perimeter side, a bottom portion, and a top portion, the body further comprising a liquid test sample mixing chamber and a reaction chamber, the liquid test sample mixing chamber and the reaction chamber being separated by a filter, the reaction chamber further comprising at least two sample wells and at least two sample reaction chambers wherein at least two diagnostic assays are performed on a patient's liquid test sample; an inlet for introducing a liquid test sample into the liquid test sample mixing chamber; and a buffer tray, the buffer tray comprising a container having a buffer well containing at least one buffer, the buffer tray further comprising a flexible cover removably affixed to a top portion of the container to selectively seal the at least one buffer in the buffer tray; and introducing the liquid test sample via the inlet of the reaction cassette into the liquid test sample mixing chamber; removing the flexible cover thereby introducing the at least one buffer from the buffer well into the liquid test sample mixing chamber, whereby the at least one buffer mixes with the liquid test sample to thereby form a mixed liquid test sample in the liquid test sample mixing chamber; rotating the reaction cassette about the horizontal axis such that the mixed liquid test sample is introduced from the liquid test sample mixing chamber through the filter into to the reaction chamber; additionally rotating the reaction cassette about the horizontal axis such that the mixed liquid test sample is separated into at least two separate subsamples, the at least two subsamples comprising at least a first subsample and a second subsample of substantially equal volumes, the at least two separate subsamples of substantially equal volume being contained separately in each of the at least two sample wells; oscillating the reaction cassette about such horizontal axis to agitate the at least two separate subsamples so as to thereby result in the flow of the at least two separate subsamples from the at least two sample wells through the at least two bubble pits into the at least two sample reaction chambers, whereby the first subsample of the at least two subsamples contacts and reacts with a first reaction zone contained within a first sample reaction chamber of the at least two sample reaction chambers and the second subsample of the at least two subsamples contacts and reacts with a second reaction zone contained within a second sample reaction chamber of the at least two sample reaction chambers; measuring a first detectable response in the first subsample that has reacted with the first reaction zone to determine the presence of at least one analyte present in the first subsample; and measuring a second detectable response in the second subsample that has reacted with the second reaction zone to determine the presence of at least one analyte present in the second subsample.

The method, wherein the patient's liquid test sample is selected from the group consisting of whole blood and urine.

The method, wherein patient's liquid test sample is a 1 microliter volume of whole blood.

The method, wherein the at least two diagnostic assays performed within the at least two sample reaction chambers are the same diagnostic assays.

The method, wherein the at least two diagnostic assays performed within the at least two sample reaction chambers are different diagnostics assays.

The method, wherein the reaction chamber comprises at least three sample reaction chambers.

The method, wherein a concentration of at least one analyte present in the first subsample is detected via the measurement of the first detectable response.

The method, wherein a concentration of at least one analyte present in the second subsample is detected via the measurement of the second detectable response.

Thus, in accordance with the presently disclosed and claimed inventive concept(s), there have been provided devices, kits, and methods for conducting multiple diagnostic assays, such as, analyte(s) detection assays, on a patient's single liquid test sample. As described herein, the presently disclosed and claimed inventive concept(s) relate to embodiments of a modified reaction cassette that is capable of separating a patient's liquid test sample into substantially equal-volume subsamples, whereby the same or different diagnostic assays are conducted on each subsample within the reaction cassette, as well as kits and methods of use related thereto. is created that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A reaction cassette for the conductance of at least one diagnostic assay, the reaction cassette comprising:
a body, the body comprising a top perimeter side, a bottom perimeter side, a first perimeter side, a second perimeter side, a bottom portion, and a top portion, the body further comprising a liquid test sample mixing chamber and a reaction chamber, the reaction chamber further comprising at least two sample wells, at least two bubble pits, and at least two sample reaction chambers wherein at least two diagnostic assays are performed on a patients liquid test sample;
an inlet for introducing a liquid test sample into the liquid test sample mixing chamber; and
a buffer tray, the buffer tray comprising a container having a buffer well containing at least one buffer, the buffer tray further comprising a flexible cover removably affixed to a top portion of the container to selectively seal the at least one buffer in the buffer tray;
wherein each of the at least two sample wells are connected to a respective one of the at least two sample reaction chambers through a respective one of the at least two bubble pits such that the liquid test sample is retained at each of the at least two bubble pits until the reaction cassette is agitated and then the liquid test sample passes through each of the at least two bubble pits to their respective one of the at least two reaction chambers.

2. The reaction cassette of claim 1, wherein the patient's liquid test sample is selected from the group consisting of whole blood and urine.

3. The reaction cassette of claim 2, wherein patient's liquid test sample is a 1 microliter volume of whole blood.

4. The reaction cassette of claim 1, wherein the at least two diagnostic assays performed within the at least two sample reaction chambers are the same diagnostic assays.

5. The reaction cassette of claim 1, wherein the at least two diagnostic assays performed within the at least two sample reaction chambers are different diagnostics assays.

6. The reaction cassette of claim 1, wherein the reaction chamber comprises at least three sample reaction chambers.

7. The reaction cassette of claim 1, wherein each of the at least two sample reaction chambers further comprise at least one solid reagent zone positioned within each of the at least two sample reaction chambers, each of the at least one solid reagent zone comprising at least one solid analytical reagent.

8. An analytical reaction kit, the kit comprising:
a reaction cassette, the reaction cassette comprising:
- a body, the body comprising a top perimeter side, a bottom perimeter side, a first perimeter side, a second perimeter side, a bottom portion, and a top portion, the body further comprising a liquid test sample mixing chamber and a reaction chamber, the reaction chamber further comprising at least two sample wells, at least two bubble pits and at least two sample reaction chambers wherein at least two diagnostic assays are performed on a patient's liquid test sample;
- an inlet for introducing a liquid test sample into the liquid test sample mixing chamber; and
- a buffer tray, the buffer tray comprising a container having a buffer well containing at least one buffer, the buffer tray further comprising a flexible cover removably affixed to a top portion of the container to selectively seal the at least one buffer in the buffer tray; and
- a capillary, the capillary capable of being partially inserted into the inlet of the reaction cassette to thereby introduce a liquid test sample into the liquid test sample mixing chamber of the reaction cassette;
- wherein each of the at least two sample wells are connected to a respective one of the at least two sample reaction chambers through a respective one of the at least two bubble pits such that the liquid test sample is retained at each of the at least two bubble pits until the reaction cassette is agitated and then the liquid test sample passes through each of the at least two bubble pits to their respective one of the at least two reaction chambers.

9. The analytical reaction kit of claim 8, wherein the patient's liquid test sample is selected from the group consisting of whole blood and urine.

10. The analytical reaction kit of claim 9, wherein patient's liquid test sample is a 1 microliter volume of whole blood.

11. The analytical reaction kit of claim 8, wherein the at least two diagnostic assays performed within the at least two sample reaction chambers are the same diagnostic assays.

12. The analytical reaction kit of claim 8, wherein the at least two diagnostic assays performed within the at least two sample reaction chambers are different diagnostics assays.

13. The analytical reaction kit of claim 8, wherein the reaction chamber comprises at least three sample reaction chambers.

14. The analytical reaction kit of claim 8, wherein each of the at least two sample reaction chambers further comprise at least one solid reagent zone positioned within each of the at least two sample reaction chambers, each of the at least one solid reagent zone comprising at least one solid analytical reagent.

15. A method for performing at least two diagnostic assays on a patient's single liquid test sample, the method comprising the steps of:
providing a reaction cassette having a substantially horizontal axis of rotation, a reaction cassette, the reaction cassette comprising:
- a body, the body comprising a top perimeter side, a bottom perimeter side, a first perimeter side, a second perimeter side, a bottom portion, and a top portion, the body further comprising a liquid test sample mixing chamber and a reaction chamber, the reaction chamber further comprising at least two sample wells, at least two bubble pits and at least two sample reaction chambers wherein at least two diagnostic assays are performed on a patient's liquid test sample;
- an inlet for introducing a liquid test sample into the liquid test sample mixing chamber; and
- a buffer tray, the buffer tray comprising a container having a buffer well containing at least one buffer, the buffer tray further comprising a flexible cover removably affixed to a top portion of the container to selectively seal the at least one buffer in the buffer tray;
- wherein each of the at least two sample wells are connected to a respective one of the at least two sample reaction chambers through a respective one of the at least two bubble pits such that the liquid test sample is retained at each of the at least two bubble pits until the reaction cassette is agitated and then the liquid test sample passes through each of the at least two bubble pits to their respective one of the at least two reaction chambers; and introducing the liquid test sample via the inlet of the reaction cassette into the liquid test sample mixing chamber;

removing the flexible cover thereby introducing the at least one buffer from the buffer well into the liquid test sample mixing chamber, whereby the at least one buffer mixes with the liquid test sample to thereby form a mixed liquid test sample in the liquid test sample mixing chamber;

rotating the reaction cassette about the horizontal axis such that the mixed liquid test sample is introduced from the liquid test sample mixing chamber through the filter into to the reaction chamber;

additionally rotating the reaction cassette about the horizontal axis such that the mixed liquid test sample is separated into at least two separate subsamples, the at least two subsamples comprising at least a first subsample and a second subsample of substantially equal volumes, the at least two separate subsamples of substantially equal volume being contained separately in each of the at least two sample wells;

oscillating the reaction cassette about such horizontal axis to agitate the at least two separate subsamples so as to thereby result in the flow of the at least two separate subsamples from the at least two sample wells into the at least two sample reaction chambers, whereby the first subsample of the at least two subsamples contacts and reacts with a first reaction zone contained within a first sample reaction chamber of the at least two sample reaction chambers and the second subsample of the at least two subsamples contacts and reacts with a second reaction zone contained within a second sample reaction chamber of the at least two sample reaction chambers;

measuring a first detectable response in the first subsample that has reacted with the first reaction zone to determine the presence of at least one analyte present in the first subsample; and measuring a second detectable response in the second subsample that has reacted with the second reaction zone to determine the presence of at least one analyte present in the second subsample.

16. The method of claim 15, wherein the patient's liquid test sample is selected from the group consisting of whole blood and urine.

17. The method of claim 16, wherein patient's liquid test sample is a 1 microliter volume of whole blood.

18. The method of claim 15, wherein the at least two diagnostic assays performed within the at least two sample reaction chambers are the same diagnostic assays.

19. The method of claim 15, wherein the at least two diagnostic assays performed within the at least two sample reaction chambers are different diagnostics assays.

20. The method of claim 15, wherein the reaction chamber comprises at least three sample reaction chambers.

* * * * *